United States Patent
Haught et al.

(10) Patent No.: US 8,691,190 B2
(45) Date of Patent: Apr. 8, 2014

(54) ORAL CARE COMPOSITIONS WITH IMPROVED SWEETNESS

(75) Inventors: John Christian Haught, West Chester, OH (US); Eva Schneiderman, Mason, OH (US); Lowell Alan Sanker, Mason, OH (US); Robert Leslie Swaine, Jr., Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 26 days.

(21) Appl. No.: 13/248,342

(22) Filed: Sep. 29, 2011

(65) Prior Publication Data

US 2012/0082630 A1 Apr. 5, 2012

Related U.S. Application Data

(60) Provisional application No. 61/388,753, filed on Oct. 1, 2010.

(51) Int. Cl.

| | |
|---|---|
| *A23L 1/236* | (2006.01) |
| *A23L 1/29* | (2006.01) |
| *A23L 2/60* | (2006.01) |
| *A61K 8/27* | (2006.01) |
| *A61Q 11/00* | (2006.01) |

(52) U.S. Cl.
USPC ................................ 424/49; 424/58; 426/548

(58) Field of Classification Search
None
See application file for complete search history.

(56) References Cited

U.S. PATENT DOCUMENTS

| | | | |
|---|---|---|---|
| 7,851,000 B2 | 12/2010 | Boghani et al. | |
| 7,851,006 B2 | 12/2010 | Bingley et al. | |
| 7,879,376 B2 | 2/2011 | Boghani et al. | |
| 2007/0190086 A1 * | 8/2007 | Sorensen | 424/401 |
| 2008/0317923 A1 | 12/2008 | Ley et al. | |
| 2009/0004360 A1 | 1/2009 | Bingley et al. | |
| 2009/0110648 A1 | 4/2009 | Cedeno | |

FOREIGN PATENT DOCUMENTS

WO  WO 2008049256 A1 *  5/2008

OTHER PUBLICATIONS

Baraldi, Pier Giovanni et al., "Transient Receptor potential Ankyrin 1 (TRPA1) Channel as Emerging Target for Novel Analgesics and Anti-Inflammatory Agents", Journal of Medicinal Chemistry Perspective, DOI: 10.1021/jm100062h.

* cited by examiner

*Primary Examiner* — Frederick Krass
*Assistant Examiner* — Michael P Cohen
(74) *Attorney, Agent, or Firm* — Armina E. Stricklin

(57) ABSTRACT

The present invention is directed to improved sweetener compositions and oral care compositions, especially those in the form of a toothpaste or oral/dental rinse, comprising the same. The sweetener composition comprises a combination of saccharin, sucralose and a rebaudioside, or sweeteners of similar sucrose equivalence and type, preferably in a ratio of about 1:about 1: about 2. The sweetener composition of the invention was found to significantly improve the taste profile, long lasting freshness and clean feel of oral care compositions and to deliver an in-use sweetness that was more natural and pleasant than artificial sweeteners alone.

13 Claims, No Drawings

ORAL CARE COMPOSITIONS WITH IMPROVED SWEETNESS

CROSS REFERENCE TO RELATED APPLICATION

This application claims the benefit of U.S. Provisional Application No. 61/388,753, filed on Oct. 1, 2010, which is herein incorporated by reference.

FIELD OF THE INVENTION

The present invention relates to sweetener compositions, oral care compositions and methods of improving the sweetness of oral care compositions.

BACKGROUND OF THE INVENTION

As a sensation, sweetness is generally recognized as a perception of sucrose and artificial sweeteners thus have ratings in terms of sucrose equivalents. There are a wide variety of compounds that enhance sweetness. Although naturally-occurring carbohydrate sweeteners, such as sucrose, are the most widely used sweeteners they suffer from the disadvantages of high cost, high caloric content, and the promotion of tooth decay. Artificial sweeteners have been designed that overcome these problems but they are sometimes rejected by the consumer for not having a sufficiently "sucrose-like" taste. Artificial sweeteners have different sweetness profiles from that of sucrose and often suffer from side effects such as delays in the onset of sweetness perception and/or unpleasant aftertastes.

Due to their contribution to tooth decay, the use of natural sweeteners, such as sucrose or high fructose corn syrup, to provide superior sweetness characteristics in oral care compositions is problematic. To reduce the tooth decay contribution, artificial sweeteners are often employed to provide sweetness though they may have undesirable tastes to consumers such as delayed sweetness onset; lingering sweet aftertaste; bitter, metallic or astringent taste; and/or dryness. For example, the sweet tastes of natural and/or synthetic high-potency sweeteners are slower in onset and longer in duration than the sweet taste produced by sugar and thus change the taste balance of a food composition. Because of these differences, use of a natural high-potency sweetener to replace a bulk sweetener, such as sugar, in a food or beverage, causes an unbalanced temporal and/or flavor profile. In addition to the difference in temporal profile, high-potency sweeteners generally exhibit (i) lower maximal response than sugar, (ii) off tastes including bitter, metallic, cooling, astringent, licorice-like taste, etc., and/or (iii) sweetness which diminishes on iterative tasting. It is well known to those skilled in the art of food/beverage formulation that changing the sweetener in a composition requires re-balancing of the flavor and other taste components (e.g., acidulants). If the taste profile of natural and synthetic high-potency sweeteners could be modified to impart specific desired taste characteristics to be more sugar-like, the type and variety of compositions that may be prepared with that sweetener would be significantly expanded. Accordingly, it would be desirable to selectively modify the taste characteristics of natural and synthetic high-potency sweeteners.

The aftertaste of artificial sweeteners in oral care products is particularly problematic in that many of the ingredients in oral care compositions have negative taste attributes of their own. Whilst flavor has been used as a compensator to disguise the off-tasting materials, including the sweetener, flavor itself can impart bitterness when used at too high a level, requiring yet more sweetener to overcome the flavor. The end result can be a formula that is too bitter, too sweet, imparts a negative aftertaste or is simply excessively costly. The object of this invention is to provide a novel combination of sweeteners that overcomes the aforementioned negative attributes. This combination provides a longer lasting freshness, clean feel, reduction in bitterness, and taste impression than do any of the sweeteners alone.

Some relevant disclosures in relating to the use of sweetener combinations include: EP 658 340 A1 discloses offsetting the bitterness of betaine surfactants with a combination of saccharin, or a saccharin alternative, and another sweetening agent such as thaumatin or stevioside. The document does not teach the use of triple combinations of sweeteners where saccharin use was reduced, such as described herein.

In US 2007/0116831 A1 (Prakash, Dubois) disclose the use in a dental composition of a high potency sweetener composition comprising a natural high potency sweetener such as rebaudioside A and/or a synthetic high potency sweetener, such as sucralose, in combination with a 'sweet taste improving composition' and a dental active. Their objective was to create a more sugar-like profile. In US 2009/0053378 A1 Prakash et al. build on US 2007/0116831 A1 by further disclosing the inclusion of a sweetness enhancer, such as an aryl carboxylic acid derivative. Neither of these documents teaches the use of the combinations of sweeteners described herein.

US 2009/0004360 A1 (Bingley) is also concerned with using a sweetener modifier, in this case a (di)hydroxybenzoic acid, to modify sweetener profiles. It does not teach the use of multiple sweeteners.

US 2007/0178123 A1 (Levenson et al.) relates to flavor enhancing compositions for products for the treatment of cough. It discloses combinations of neotame and sucralose. EP 1 869 986 (Schwarz, Rathjen) discloses edible compositions said to have the taste profile of sucrose but which comprise a combination of isomaltulose, acesulfame K and another high intensity sweetener such as sucralose.

WO 2009/086049 (Catani, Liao) discloses a sweetening composition comprising a combination of sucralose and a purified extract of stevia comprising rebaudiosides and dulcosides. Within certain ratios of the sucralose to stevia, synergism of the sweetening intensity was observed. The document does not disclose particular combinations of the sucralose and stevia with other sweeteners.

U.S. Pat. No. 4,915,969 (Beyts) reveals sweetening synergy of sucralose and cyclamate within beverages.

JP 2002-171930 (Morita et al.) reports an excellent degree of sweetness and sweetness quality from combinations of sucralose, stevia and acesulfame K.

Despite this progress in developing new sweetener combinations with a more sucrose-like profile, there is still a need for oral, particularly dentifrice and rinse, compositions that include sweetness optimized compositions. It would be desirable to develop a sweetness composition that allows the quantity of natural or artificial sweetener in an orally delivered product to be reduced or optimized, thereby reducing the off-tastes associated with specific raw materials in the orally delivered product, but which avoids adverse effects on flavor. In particular, there is a need for a sweetener composition that is capable providing high sucrose equivalence, as well as modifying the perception of sweet flavor of the sweetener, the aftertaste of the sweetener, the sweetness onset period of the sweetener, the sweetness peak period of the sweetener and/or the sweetness decay period of the sweetener.

SUMMARY OF THE INVENTION

The present invention is directed to improved sweetener compositions and oral care compositions, especially those in the form of a toothpaste or oral/dental rinse, comprising the same. More specifically, the invention relates to a sweetener composition and an oral composition comprising the same wherein the sweetener composition comprises Sweetener A, Sweetener B and Sweetener C, wherein Sweetener A is an artificial sweetener having 250-350 sucrose equivalents, Sweetener B is an artificial sweetener having 500-600 sucrose equivalents and Sweetener C is a natural sweetener with 0.5-400 sucrose equivalents. The preferred embodiments of Sweeteners A, B and C are respectively saccharin, sucralose and a rebaudioside. Preferably Sweeteners A, B and C are in a (0.5-2):(0.5-2):2 ratio. In the most preferred embodiment the sweetener composition comprises a combination of saccharin, sucralose and a rebaudioside in a ratio of about 1:1:2.

The invention further relates to a method of improving the sweetness of an oral care composition comprising adding the sweetener composition of the invention to the oral care composition.

DETAILED DESCRIPTION OF THE INVENTION

All percentages and ratios used hereinafter are by weight of total composition, unless otherwise indicated. All percentages, ratios, and levels of ingredients referred to herein are based on the actual amount of the ingredient and do not include solvents, fillers, or other materials with which the ingredient may be combined as a commercially available product, unless otherwise indicated. All measurements referred to herein are made at 25° C. (i.e. room temperature) unless otherwise specified.

As used herein, the word "about" means+/−10 percent. As used herein, the word "include," and its variants, are intended to be non-limiting, such that recitation of items in a list is not to the exclusion of other like items that may also be useful in the materials, compositions, devices, and methods of this invention.

By "oral care composition" herein is meant a product which, in the ordinary course of usage, is not immediately swallowed for purposes of systemic administration of particular therapeutic agents, but is rather retained in the oral cavity for a sufficient time, or has sufficient extent of contact with the tongue, to experience its taste. Applicable oral care compositions include personal health care products (such as cough syrups, cough drops and the like), confections, foods and beverages (such as chewing gum, soda and the like). The preferred oral care compositions are not intended as nutritional foods and may be in various forms including a tooth paste or gel, subgingival gel, mouth rinse, mousse, foam, mouth spray, lozenge, chewable tablet, lozenge, chewing gum or denture care product. The oral care composition may also be incorporated onto strips or films for direct application or attachment to oral surfaces. In the preferred embodiments the oral care composition comprises a surfactant or other therapeutic active directed at the oropharynx, in particular the oral cavity.

The term "dentifrice", as used herein, includes paste, gel, or liquid formulations unless otherwise specified. The term "teeth", as used herein, refers to natural teeth as well as artificial teeth or dental prosthesis.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

Sweeteners

References to sweeteners herein also include reference to their usual salts; for example, the term 'saccharin' includes sodium saccharin and 'acesulfame' includes the potassium salt, acesulfame K. As is commonly understood in the art, sweeteners can be characterized in terms of their sucrose equivalence, representing the ratio of the weight of sucrose delivering a certain amount of sweetness to the weight of sweetener required to deliver the same amount of sweetness, as determined by an expert panel matching the sweetness intensity of solutions of the sweetener to that of stock solutions of sucrose. Since the sucrose equivalence can depend on the concentration of sucrose being matched, the sucrose equivalents herein are 10% sucrose equivalents. Thus if a 0.1% solution of a sweetener delivers the same sweetness intensity as a 10% sucrose solution, that sweetener has a 10% sucrose equivalence of 100 (10/0.1).

In one aspect the present invention relates to a sweetener composition wherein the sweetener composition comprises Sweetener A, Sweetener B and Sweetener C, wherein Sweetener A is an artificial sweetener having from 250 to 350 sucrose equivalents, Sweetener B is an artificial sweetener having from 500 to 600 sucrose equivalents and Sweetener C is a natural sweetener having from 0.5 to 400 sucrose equivalents.

Preferably Sweeteners A, B and C are in a (0.5-2):(0.5-2):2 ratio. In one embodiment the ratio of Sweetener A to Sweetener B is from 0.5:1 to 2:1, preferably from 0.8:1 to 1.5:1. In one embodiment the ratio of Sweetener A to Sweetener C is from 0.3:1 to 0.9:1, preferably from 0.3:1 to 0.7:1.

Sweetener A is a high intensity sweetener preferably selected from the group consisting of saccharin, alitame, aspartame, neotame, cyclamate and mixtures thereof. These sweeteners are typically measured with a 10% sucrose equivalence of from 250-350. Sweetener A is most preferably saccharin.

Sweetener B is a high intensity sweetener preferably selected from the group consisting of trichloro-sucrose (sucralose), acesulfame, neohesperidine DC, thaumatin, glycyrrhizin, mogroside IV, mogroside V, cyclocarioside I,N-[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methyl-butyl]-L-α-aspartyl]-L-phenylalanine 1-methyl ester, N-[N-[3-(3-methoxy-4-hydroxyphenyl)-propyl]-L-α-aspartyl]-L-phenylalanine 1-methyl ester, and mixtures thereof. These sweeteners have a more intense sweetness than the Sweetener A type and are typically measured with a 10% sucrose equivalence of from 500-600. Sweetener B is most preferably sucralose.

Sweetener C is a naturally derived glycoside or polyol sweetener preferably selected from the group consisting of steviolglycosides, rebaudioside A, rebaudioside B, rebaudioside C, rebaudioside D, rebaudioside E, rebaudioside F, dulcoside A, dulcoside B, rubusoside, stevia, stevioside, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobtain, baiyanoside, osladin, polypodoside A, pterocaryoside A, pterocaryoside B, mukurozioside, phlomisoside I, periandrin I, abrusoside A and mixtures thereof. Additionally, Sweetener C could be selected from one or more of the following naturally derived sources, for example, polyols such as xylitol, erythritol, maltitol, mannitol, and sorbitol or L-arabinose, inulin, dextrin, raffinose, trehalose, tagitose, or tagitol. These sweeteners are typically measured with a 10% sucrose equivalence of from 0.5-400. In particularly desirable embodiments of the present invention, Sweetener C comprises rebaudioside A in combination with one or more of rebaudioside B, rebaudioside C, rebaudioside F, rebaudioside F, stevioside, steviolbioside, or dulcoside A. In a preferred embodiment herein Sweetener C comprises at least 70% rebaudioside A or xylitol. REBIANA is a trade name for a high purity source of rebaudioside A commercialized by Cargill, Inc. and The Coca-Cola Company. It is a crystalline diterpene glycoside, about 300× sweeter than sucrose. Xylitol is a polyol made by Cargill.

The sweetener compositions herein can further comprise edible carrier materials to improve the flow properties of the sweetener compositions. These edible carrier materials can comprise bulk sweetener materials, in particular crystalline sugar alcohols which, though they may impart some sweetness have a much lower sweetness intensity than the sweeteners of the present invention. Additionally, a flavor enhancer such as glucono-δ-lactone or a hydroxybenzoic acid can be added to the sweetener composition.

In preferred embodiments herein the sweetener compositions herein comprise, in total, from 20% to 100%, preferably from 50% to 100% of Sweeteners A, B and C.

Oral Care Compositions

A further aspect the present invention relates to oral care compositions comprising the inventive sweetener composition. The oral care compositions can comprise from 0.001% to 4%, preferably from 0.01% to 3% of the inventive sweetener composition.

It is highly desirable that consumer products for use in cleaning and care of the oral cavity impart a fresh and clean feeling as this provides consumers with a signal of continuing freshness and cleanliness. In addition to the feeling of cleanliness, consumers typically want to benefit from therapeutic oral care actives, like anti-tartar agents for example, through their oral care regimen. Oral care compositions are often made up of a combination of components which can include carrier materials, surfactants, flavors, sensates, colorants, actives, and other additives. The ability to formulate a consumer acceptable oral care composition, however, raises challenges as many of the components used to impart a flavor, deliver a benefit, or that are part of the base for the oral care composition add unwanted tastes and/or sensations along with the targeted benefit for which they are added. Thus, formulating oral care compositions can be a balancing act between acceptable flavor and acceptable benefits.

Oral Care Carrier Materials

Oral care carrier materials generally represent anywhere from 25% to 95% of the oral care composition by weight. Examples of materials which can act as a carrier material include water, glycerin, sorbitol, polyethylene glycols having a molecular weight of less than 50,000, propylene glycol and other edible polyhydric alcohols, ethanol, or combinations thereof. Many of these carrier materials also act as humectants which stop toothpastes drying out. Of these carrier materials, examples of some which provide an unwanted taste within an oral care composition are propylene glycol and ethanol. The unwanted tastes often associated with these types of materials are bitterness, burning, astringency, and/or earthy or dirty tastes.

Surfactants

Another component of an oral care composition, particularly a dentifrice, can be a surfactant. Surfactants are generally included in an oral care composition in a range of 1% to 15%. The surfactant may be anionic, nonionic, amphoteric, zwitterionic, cationic, or combinations thereof. Anionic surfactants useful herein include, for example, the water-soluble salts of alkyl sulfates having from 8 to 20 carbon atoms in the alkyl radical and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzenesulfonate. Combinations of anionic surfactants can also be employed. In varying embodiments, the present compositions comprise an anionic surfactant at a level of from 0.25% to 9%, from 0.05% to 5%, or from 0.1% to 1%.

Another class of anionic surfactants useful here are alkyl phosphates. The surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein $Z_1$, $Z_2$, or $Z_3$ may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

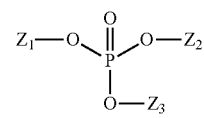

Some other agents include alkyl or alkenyl phosphate esters represented by the following structure:

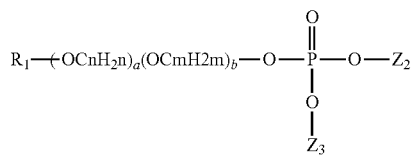

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z_2$ and $Z_3$ may be identical or different, each represents hydrogen, alkali metal, ammonium, protonated alkyl amine or protonated functional alkyl amine such as an alkanolamine, or a $R_1—(OC_nH_{2n})_a(OC_mH_{2m})_b$— group. Examples of suitable agents include alkyl and alkyl (poly)alkoxy phosphates such as lauryl phosphate; PPGS ceteareth-10 phosphate; laureth-1 phosphate; laureth-3 phosphate; laureth-9 phosphate; trilaureth-4 phosphate; $C_{12-18}$ PEG 9 phosphate; and sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Other suitable surfactants are sarcosinates, isethionates and taurates, especially their alkali metal or ammonium salts. Examples include: lauroyl sarcosinate, myristoyl sarcosinate, palmitoyl sarcosinate, stearoyl sarcosinate and oleoyl sarcosinate, or combinations thereof. Of these anionic surfactants, examples of some which provide an unwanted taste within an oral care composition include, for example, SLS, lauroyl sarcosinate, and/or fatty alcohols or acids associated with natural based surfactants. The unwanted tastes often associated with these surfactants are soapy, chemical, and/or artificial.

Zwitterionic or amphoteric surfactants useful herein include derivatives of aliphatic quaternary ammonium, phosphonium, and sulfonium compounds, in which the aliphatic radicals can be straight chain or branched, and one of the aliphatic substituents contains from 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine (CADB), and lauramidopropyl betaine. Of these surfactants, examples of some which provide an unwanted taste within an oral care composition include, for example, cocoamidopropyl betaine and lauryl betaine. The unwanted tastes often associated with these types of surfactants are soapy and chemical. These surfactants are generally included in an oral care composition in a range of 0.5% to 5%.

Cationic surfactants useful in the present invention include, for example, derivatives of quaternary ammonium compounds having one long alkyl chain containing from 8 to 18 carbon atoms such as lauryl trimethylammonium chloride; cetyl pyridinium chloride; cetyl trimethyl-ammonium bromide; cetyl pyridinium fluoride or combinations thereof. Of these surfactants, examples of some which provide an unwanted taste within an oral care composition include, for example, cetyl pyridinium chloride or chlorhexidine. The unwanted tastes often associated with these surfactants are chemical and/or antiseptic.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials.

Flavors

Another component which can be part of an oral care composition includes a flavor. Flavors are generally present in an amount of 0.4% to 3% by weight of the oral care composition. Examples of some flavors and flavor components used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups. Of these flavors, examples of some which provide an unwanted taste include, for example, citral, geranial, eucalyptol, thymol and eugenol. The unwanted tastes often associated with these types of flavors are sourness, chemical, bitter, pungent, and/or astringent.

Sensates

Another component which can be part of an oral care composition is a sensate. Sensate agents such as cooling, warming, and tingling agents are useful to deliver signals to the consumer. Sensates are generally used in amounts of 0.001% to 0.8% of the oral care composition. The most well-known cooling sensate compound is menthol, particularly 1-menthol, which is found naturally in peppermint oil. At high levels menthol can provide a bitter taste and is sometimes associated with disagreeable notes described as earthy, camphor, musty, etc.

Among synthetic coolants, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide. An example of a synthetic carboxamide coolant that is structurally unrelated to menthol is N,2,3-trimethyl-2-isopropylbutanamide. Additional exemplary synthetic coolants include alcohol derivatives such as 3-1-menthoxy-propane-1,2-diol, isopulegol, p-menthane-3,8-diol; menthone glycerol acetal; menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3(2H)-furanone (DMPF); icilin (also known as AG-3-5, chemical name 1[2-hydroxyphenyl]-4-[2-nitrophenyl]-1,2,3,6-tetrahydropyrimidine-2-one) described in Wei et al., J. Pharm. Pharmacol. (1983), 35:110-112.

Of these cooling sensates, examples of some which provide an unwanted taste include, for example, menthol and menthone. The unwanted tastes often associated with these cooling sensates include burning, chemical, and/or medicinal.

Some examples of warming sensates include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of from 0.05% to 2%.

Examples of some tingling sensates include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof. Tingling sensates are generally included in an oral care composition at a level of 0.0005% to 1%. Of these tingling sensates, examples of some which provide an unwanted taste within an oral care composition include, for example, jambu and saanshool. The unwanted taste(s) often associated with these tingling sensates include a peppery, bitter, and/or metallic taste.

Sweeteners

References to sweeteners herein also include reference to their usual salts; for example, the term 'saccharin' includes sodium saccharin and 'acesulfame' includes the potassium salt, acesulfame K. As is commonly understood in the art, sweeteners can be characterized in terms of their sucrose equivalence, representing the ratio of the weight of sucrose delivering a certain amount of sweetness to the weight of sweetener required to deliver the same amount of sweetness, as determined by an expert panel matching the sweetness intensity of solutions of the sweetener to that of stock solutions of sucrose. Since the sucrose equivalence can depend on the concentration of sucrose being matched, the sucrose equivalents herein are 10% sucrose equivalents. Thus if a 0.1% solution of a sweetener delivers the same sweetness intensity as a 10% sucrose solution, that sweetener has a 10% sucrose equivalence of 100 (10/0.1).

In one aspect the present invention relates to a sweetener composition wherein the sweetener composition consists of Sweetener A, Sweetener B and Sweetener C in a (0.5-1):(0.5-1):(1-3) ratio, wherein Sweetener A is an artificial sweetener having from 250 to 350 sucrose equivalents, Sweetener B is an artificial sweetener having from 500 to 600 sucrose equivalents and Sweetener C is a natural sweetener having from 0.5 to 400 sucrose equivalents. Sweetener A is a high intensity sweetener preferably selected from the group consisting of saccharin, alitame, aspartame, neotame, cyclamate and mixtures thereof. These sweeteners are typically measured with a 10% sucrose equivalence of from 250-350. Sweetener A is most preferably saccharin.

Sweetener B is a high intensity sweetener preferably selected from the group consisting of trichloro-sucrose (sucralose), acesulfame, neohesperidine DC, thaumatin, glycyrrhizin, mogroside IV, mogroside V, cyclocarioside I, N-[N-[3-(3-hydroxy-4-methoxyphenyl)propyl]-L-α-aspartyl]-L-phenylalanine 1-methyl ester, N-[N-[3-(3-hydroxy-4-methoxyphenyl)-3-methyl-butyl]-L-α-aspartyl]-L-phenylalanine 1-methyl ester, N-[N-[3-(3-methoxy-4-hydroxyphenyl)-propyl]-L-α-aspartyl]-L-phenylalanine 1-methyl ester, and mixtures thereof. These sweeteners have a more intense sweetness than the Sweetener A type and are typically measured with a 10% sucrose equivalence of from 500-600. Sweetener B is most preferably sucralose.

Sweetener C is a naturally derived glycoside sweetener preferably selected from the group consisting of steviolglycosides, rebaudioside A, rebaudioside B, rebaudioside C, rebaudioside D, rebaudioside E, rebaudioside F, dulcoside A, dulcoside B, rubusoside, stevia, stevioside, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobtain, baiyanoside, osladin, polypodoside A, pterocaryoside A, pterocaryoside B, mukurozioside, phlomisoside I, periandrin I, abrusoside A and mixtures thereof. These sweeteners are typically measured with a 10% sucrose equivalence of from 0.5-400. In particularly desirable embodiments of the present invention, Sweetener C comprises rebaudioside A in combination with one or more of rebaudioside B, rebaudioside C, rebaudioside F, rebaudioside F, stevioside, steviolbioside, or dulcoside A or the polyol xylitol. Sweetener C is most preferably rebaudioside A or xylitol. REBIANA is a trade name for a high purity source of rebaudioside A commercialized by Cargill, Inc. and The Coca-Cola Company. It is a crystalline diterpene glycoside, about 300× sweeter than sucrose. Xylitol is a naturally occurring sugar alcohol and is also supplied by Cargill.

Additionally, a flavour enhancer such as glucono-δ-lactone can be added to the sweetener composition.

Colorants

Additionally, colorants can form part of an oral care composition. Colorants are generally present in an amount of 0.001% to 0.5% by weight of the oral care composition. Examples of some colorants used in oral care compositions include D&C Yellow No. 10, FD&C Blue No. 1, FD&C Red No. 40, D&C Red No. 33 and combinations thereof. Levels of the colorant may range from 0.0001% to 0.1%. In one embodiment, the colorant is in an amount from 0.001% to 0.01% by weight of the oral care composition. Of these colorants, an example of a colorant which provides an unwanted taste includes, for example, D&C Red No. 33. The unwanted tastes often associated with this colorant are metallic and/or chemical.

Actives

An additional component which can be included in an oral care composition includes oral care actives. Oral care actives are generally present in an amount of 0.0001% to 8%. Some examples of oral care actives include anticaries agents, antimicrobial agents, antitartar agents, bad breath reduction agents, and bleaching agents. Anticaries agents are generally used in an amount of 0.01% to 3.0%. It is common to have a fluoride compound present in dentifrices and other oral compositions in an amount sufficient to give a fluoride ion concentration in the composition of from 0.0025% to 5.0% by weight to provide anticaries effectiveness. In one embodiment, the fluoride concentration is from 0.005% to 2.0% by weight. A wide variety of fluoride ion-yielding materials can be employed as sources of soluble fluoride in the present compositions and methods. Examples of suitable fluoride ion-yielding materials are found in U.S. Pat. No. 3,535,421 to Briner et al. and U.S. Pat. No. 3,678,154 to Widder et al. Representative fluoride ion sources include: stannous fluoride, sodium fluoride, potassium fluoride, amine fluoride, sodium monofluorophosphate, indium fluoride, amine fluorides such as Olaflur, and many others. In one embodiment, the anticaries agent comprises stannous fluoride in an amount of 0.454%. In another embodiment, the anticaries agent comprises sodium fluoride in an amount of 0.243%. Of these anticaries agents, examples of some which provide an unwanted taste include, for example, stannous fluoride and potassium fluoride. The unwanted tastes often associated with these anticaries agents include earthy, dirty, and/or metallic.

Another oral care active is an antimicrobial agent. One example of an antimicrobial agent is a quaternary ammonium compound. Those useful herein include, for example, those in which one or two of the substitutes on the quaternary nitrogen has a carbon chain length (typically alkyl group) from 8 to 20, typically from 10 to 18 carbon atoms while the remaining substituents (typically alkyl or benzyl group) have a lower number of carbon atoms, such as from 1 to 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetylpyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents. Other compounds include bis[4-(R-amino)-1-pyridinium]alkanes as disclosed in U.S. Pat. No. 4,206,215, Jun. 3, 1980 to Bailey. Other quaternary ammonium compounds include the pyridinium compounds. Examples of pyridinium quaternary ammonium compounds include cetylpyridinium and tetradecylpyridinium halide salts (i.e., chloride, bromide, fluoride and iodide). The quaternary ammonium antimicrobial agents can be included at levels of at least 0.035%. In other embodiments they are included from 0.045% to 1.0% or from 0.05% to 0.10% by weight of the oral care composition.

The present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, triclosan, triclosan monophosphate, and flavor oils such as thymol. Triclosan and other agents of this type are disclosed in Parran, Jr. et al., U.S. Pat. Nos. 5,015,466, and 4,894,220 to Nabi et al. These agents may be present at levels of from 0.01% to 1.5%, by weight of the dentifrice composition. Of the above antimicrobial agents, examples of some which provide an unwanted taste include, for example, chlorhexidine, triclosan, and thymol. The unwanted tastes often associated with these types of antimicrobial agents include bitter, dirty, earthy, sour, and/or astringent.

Another oral care active agent includes antitartar agents. One example of an antitartar agent is a pyrophosphate salt as a source of pyrophosphate ion. The pyrophosphate salts useful in the present compositions include, for example, the mono-, di- and tetraalkali metal pyrophosphate salts and combinations thereof. Disodium dihydrogen pyrophosphate ($Na_2H_2P_2O_7$), sodium acid pyrophosphate, tetrasodium pyrophosphate ($Na_4P_2O_7$), and tetrapotassium pyrophosphate ($K_4P_2O_7$) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying embodiments, the amount of pyrophosphate salt is from 1.5% to 15%, from 2% to 10%, or 3% to 8%, by weight of the oral care composition.

An additional example of an oral care active is a bleaching agent for whitening teeth. Examples of bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. The following amounts represent the amount of peroxide raw material, although the peroxide source may contain ingredients other than the peroxide raw material. For example, the peroxide source could be a solution a peroxide raw material and a carrier material. Generally, the present composition may contain from 0.01% to 30% of peroxide raw material. In other embodiments, the peroxide raw material is from 0.1% to 10% or from 0.5% to 5%, by weight of the oral care composition. Of these bleaching agents, examples of some which provide an unwanted taste within an oral care composition include, for example, peroxide and percarbonate. The unwanted tastes often associated with these bleaching agents include dirty, chemical, and/or sour.

Another oral care active is a bad breath reduction agent. Examples of bad breath reduction agents include copper salts and carbonyl compounds such as ascorbic acid [3-oxo-L-gulofuranolactone]; cis-jasmone [3-methyl-2-(2-pentenyl-2-cyclopentenone]; 2,5-dimethyl-4-hydroxy-3 (2H)-furanone; 5-ethyl-3-hydroxy-4-methyl-2(5H)-furanone; vanillin [4-hydroxy-3-methoxybenzaldehyde]; ethyl vanillin; anisaldehyde [4-methoxybenzaldehyde]; 3,4-methylenedioxybenzaldehyde; 3,4-dimethoxybenzaldehyde; 4-hydroxybenzaldehyde; 2-methoxybenzaldehyde; benzaldehyde; cinnamaldehyde [3-phenyl-2-propenal]; hexyl cinnamaldehyde; α-methyl cinnamaldehyde; ortho-methoxy cinnamaldehyde; or combinations thereof. Without being limited by theory, it is believed some bad breath reduction agents work as "traps" by reacting with the thiol or sulfide and forming products with less odor impact. Of these bad breath reduction agents, an example of one which provide an unwanted taste within an oral care composition include, for example, anisaldehyde. The unwanted tastes often associated with these types of bad breath reduction agents include chemical, plastic, bitter, and/or sour.

Metal Salts

Another potential component in an oral care composition is a metal salt. Metal salts have a wide range of functions from antimicrobial agents to sensitivity agents and/or buffers. In one embodiment, the metal salt comprises a zinc salt, stannous salt, potassium salt, copper salt, or a combination thereof. In a further embodiment, the zinc salt is selected from the group consisting of zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof. In another embodiment, the zinc salt comprises zinc chloride, zinc citrate, zinc gluconate, zinc lactate, zinc oxide, or combinations thereof.

In an additional embodiment, the potassium salt is selected from the group consisting of potassium nitrate, potassium citrate, potassium oxalate, potassium bicarbonate, potassium acetate, potassium chloride, and combinations thereof. In a further embodiment, the potassium salt comprises potassium nitrate, potassium citrate, potassium chloride, or combinations thereof. In an additional embodiment, the copper salt is selected from the group consisting of copper fluoride, copper chloride, copper iodide, copper chlorofluoride, copper acetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt comprises copper gluconate, copper acetate, copper glycinate, or a combination thereof.

In another embodiment, the stannous salt is selected from the group consisting of stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, stannous gluconate, and combinations thereof. In a further embodiment, the stannous salt comprises stannous fluoride, stannous chloride, stannous chloride dihydrate, stannous fluoride, stannous lactate, stannous gluconate, stannous sulfate, or a combination thereof.

In another embodiment, the strontium salt can be selected from the group comprised of: strontium chloride, strontium citrate, strontium lactate, strontium gluconate, strontium fluoride, strontium bromide, strontium nitrate, strontium oxalate, strontium carbonate, strontium iodide, strontium sulfate, strontium hydroxide, and strontium acetate.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may be included, such as the ingredients described in Majeti et al. and Prencipe et al.

Some examples of metal salts which give an off taste include zinc chloride, zinc citrate, copper gluconate, zinc gluconate, or combinations thereof. The off tastes associated with these types of metal salts are dirty, dry, earthy, metallic, sour, bitter, and astringent.

The metal salt will be present in an amount from 0.05% to 11%, by weight of the oral care composition in one embodiment. In other embodiments, the metal salts are present in an amount of from 0.5 to 7% or from 1% to 5%. In additional embodiments, the stannous salts are present in an amount of from 0.1 to 7% or from 1% to 5% or from 1.5% to 3% by weight of the oral care composition. In certain embodiments, the amount of zinc or copper salts used in the present invention can range from 0.01 to 5%. In other embodiments the amount of zinc or copper salts are from 0.05 to 4% or from 0.1 to 3.0%.

Thus, in one embodiment, the present invention is directed to a method for improving taste of an oral care composition, comprising providing an oral care composition comprising an alkyl phosphate, betaine surfactant, cetylpyridinium chloride, phosphate, polymer, metal salt, potassium salts, a peroxide, or a combination thereof and adding to the oral care composition rebiana in an amount of 0.05% to 0.4% by weight of the oral care composition, saccharin in an amount of 0.05% to 0.4% by weight of the oral care composition, and sucralose in an amount of 0.05% to 0.4% by weight of the oral care composition. In one embodiment, the metal salt comprises a zinc salt, stannous salt, potassium salt, copper salt, or a combination thereof. In another embodiment, the peroxide is selected from the group consisting hydrogen peroxide, carbamide peroxide, calcium peroxide, sodium peroxide, and combinations thereof. In an additional embodiment, the potassium salt comprises potassium nitrate and is present in an amount of from 0.01% to 5.0% by weight of the oral care composition. In another embodiment, the zinc salt comprises zinc citrate and is present in an amount from 0.05% to 5.0% by weight of the oral care composition. In another embodiment, hydrogen peroxide is present in an amount from 0.001% to 5.0% by weight of the oral care composition.

EXAMPLES

Consumer Test I

In order to show the effect of sweetener combinations on the effects of reducing the off taste of alkyl phosphates in a dentifrice, the following formulations were made and tested in a 10 person panel. The panel rated taste attributes of the following formulations. The averages of the 10 panelists for each rating were reported from during brushing until 30 minutes after brushing.

| Ingredient | Ia | Ib | Ic | Id | Ie | If | Ig | Ih | Ii |
|---|---|---|---|---|---|---|---|---|---|
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.50 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| Vanillyl Butyl Ether | | | | | 0.02 | | | | |
| WS-23 | | | 0.02 | 0.05 | 0.02 | | | | |
| WS-3 | | | 0.02 | 0.05 | 0.02 | | | | |
| MGA | | | | 0.2 | | | | | |
| Menthol | 0.52 | 0.55 | 0.56 | 0.15 | 0.58 | | | | |
| G-180 | 0.01 | 0.03 | .015 | .004 | 0.01 | 0.01 | 0.03 | .008 | 0.02 |
| Potassium Sorbate | | | | | | .004 | .008 | .004 | .004 |
| Poloxamer 407 | | | 1.0 | | 0.2 | 0.2 | 0.2 | 0.2 | 0.2 |
| Polyethylene Glycol 300 | 3.0 | 3.0 | | 3.00 | | | | | |
| Polyethylene Glycol 600 | | | 2.3 | | | | | | |
| Propylene Glycol | | | 10.0 | | | | | | |
| Sweetener | 0.46 | 0.5 | 0.45 | 0.4 | 0.58 | 0.4 | 0.4 | 0.4 | 0.4 |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.50 | 9.0 | | | | | | |
| Sodium Carbonate | | | 0.50 | | | | | | |
| NaOH 50% Soln | | | 1.74 | 2.20 | | 2.0 | 2.0 | 2.0 | 2.0 |
| SLS (27.9% soln) | 4.0 | 5.0 | 3.0 | 4.0 | 4.0 | | | 3.0 | 2.0 |
| Sodium Fluoride | | | | | | 0.243 | 0.243 | 0.243 | |
| Sodium MFP | 0.76 | 0.76 | 0.76 | 0.76 | 0.76 | | | | 0.76 |

-continued

| Ingredient | Ia | Ib | Ic | Id | Ie | If | Ig | Ih | Ii |
|---|---|---|---|---|---|---|---|---|---|
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |
| Tetra Na Pyrophosphate, Anhydrous | 2.05 | 5.05 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Alkyl Phosphate[1] | | | | | | 3.5 | 6.7 | 3.5 | 3.5 |
| Cocamidopropyl Betaine (30% soln) | | | | | | 3.5 | | | |
| Titanium Dioxide | 0.5 | | 1.0 | | 0.25 | 0.3 | 0.3 | 0.2 | 0.2 |
| TiO$_2$/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |
| Water, Purified, USP | QS | QS | QS | QS | QS | QS | QS | QS | QS |

[1]Sodium Laureth Phosphate supplied by Rhodia

Formula If had the following combinations of sweeteners:

| | Sample: | | | | | | | | |
|---|---|---|---|---|---|---|---|---|---|
| | If-1 | If-2 | If-3 | If-4 | If-5 | If-6 | If-7 | If-8 | If-9 |
| Saccharin | 0.2 | 0.1 | 0.05 | 0.2 | 0.2 | 0.2 | 0.1 | 0.1 | 0.1 |
| Sucralose | — | — | — | — | — | — | — | — | — |
| REBITANA | — | — | — | 0.2 | 0.1 | 0.05 | 0.2 | 0.1 | 0.05 |

| | Sample: | | | | | | | | |
|---|---|---|---|---|---|---|---|---|---|
| | If-10 | If-11 | If-12 | If-13 | If-14 | If-15 | If-16 | If-17 | If-18 |
| Saccharin | 0.05 | 0.05 | 0.05 | 0.1 | 0.1 | 0.1 | 0.05 | 0.05 | 0.05 |
| Sucralose | — | — | — | 0.1 | 0.1 | 0.1 | 0.01 | 0.01 | 0.01 |
| REBIANA | 0.2 | 0.1 | 0.05 | 0.2 | 0.1 | 0.05 | 0.1 | 0.1 | 0.1 |
| NHDC | — | — | — | — | — | — | 0.1 | 0.05 | 0.05 |
| Talin | — | — | — | — | — | — | — | 0.05 | 0.05 |

| | Sample: | | | | | | | | | |
|---|---|---|---|---|---|---|---|---|---|---|
| | If-19 | If-20 | If-21 | If-22 | If-23 | If-24 | If-25 | If-26 | If-27 | If-28 |
| Saccharin | 0.4 | 0.2 | — | — | — | — | — | — | — | — |
| Sucralose | — | 0.2 | — | — | — | — | — | — | — | 0.4 |
| REBIANA | — | — | — | — | — | 0.4 | — | — | — | — |
| NHDC | — | — | — | — | — | — | 0.2 | — | — | — |
| Talin | — | — | — | — | — | — | — | — | 0.2 | — |
| Acesulfame K | — | — | 0.8 | — | — | — | — | — | — | — |
| Aspartame | — | — | — | 0.21 | — | — | — | — | — | — |
| Neotame | — | — | — | — | 0.5 | — | — | — | — | — |
| Magnasweet | — | — | — | — | — | — | — | 0.02 | — | — |

The data on samples If-1 to If-28 are shown below:

| Product # | During Brushing | After Brushing | 5 min | 10 min | 15 min | 20 min | 25 min | 30 min |
|---|---|---|---|---|---|---|---|---|
| If-1 | 17.5 | 10.0 | 12.5 | 12.5 | 10.0 | 12.5 | 12.5 | 12.5 |
| If-2 | 10.0 | 2.5 | 5.0 | 10.0 | 10.0 | 5.0 | 5.0 | 2.5 |
| If-3 | 17.5 | 12.5 | 17.5 | 17.5 | 10.0 | 7.5 | 7.5 | 7.5 |
| If-4 | 34.1 | 25.0 | 22.7 | 22.7 | 22.7 | 18.2 | 15.9 | 11.4 |
| If-5 | 30.0 | 27.5 | 15.0 | 15.0 | 15.0 | 15.0 | 12.5 | 15.0 |
| If-6 | 17.5 | 15.0 | 12.5 | 10.0 | 7.5 | 2.5 | 2.5 | 2.5 |
| If-7 | 12.5 | 17.5 | 15.0 | 5.0 | 7.5 | 7.5 | 7.5 | 10.0 |
| If-8 | 16.7 | 16.7 | 13.9 | 11.1 | 11.1 | 8.3 | 8.3 | 8.3 |
| If-9 | 15.0 | 15.0 | 17.5 | 17.5 | 17.5 | 17.5 | 12.5 | 15.0 |
| If-10 | 20.0 | 12.5 | 15.0 | 15.0 | 15.0 | 7.5 | 7.5 | 5.0 |
| If-11 | 18.2 | 18.2 | 20.5 | 9.1 | 2.3 | 2.3 | 2.3 | 2.3 |
| If-12 | 16.7 | 11.1 | 8.3 | 5.6 | 5.6 | 2.8 | 5.6 | 2.8 |
| If-13 | 45.0 | 45.0 | 42.5 | 40.0 | 37.5 | 30.0 | 27.5 | 27.5 |
| If-14 | 32.5 | 30.0 | 25.0 | 22.5 | 10.0 | 10.0 | 10.0 | 10.0 |

-continued

| Product # | During Brushing | After Brushing | 5 min | 10 min | 15 min | 20 min | 25 min | 30 min |
|---|---|---|---|---|---|---|---|---|
| If-15 | 38.9 | 27.8 | 25.0 | 19.4 | 16.7 | 13.9 | 8.3 | 8.3 |
| If-16 | 27.3 | 45.5 | 40.9 | 27.3 | 18.2 | 13.6 | 13.6 | 13.6 |
| If-17 | 17.5 | 25.0 | 17.5 | 15.0 | 15.0 | 12.5 | 10.0 | 10.0 |
| If-18 | 25.0 | 25.0 | 27.8 | 27.8 | 27.8 | 22.2 | 22.2 | 22.2 |
| If-19 | 25.0 | 27.5 | 27.5 | 25.0 | 22.5 | 10.0 | 7.5 | 7.5 |
| If-20 | 27.5 | 35.0 | 32.5 | 35.0 | 25.0 | 20.0 | 20.0 | 15.0 |
| If-21 | 20.0 | 20.0 | 22.5 | 17.5 | 12.5 | 12.5 | 10.0 | 10.0 |
| If-22 | 5.0 | 7.5 | 5.0 | 2.5 | 2.5 | 2.5 | 2.5 | 2.5 |
| If-23 | 10.0 | 7.5 | 5.0 | 7.5 | 5.0 | 7.5 | 5.0 | 5.0 |
| If-24 | 20.0 | 20.0 | 17.5 | 17.5 | 10.0 | 7.5 | 10.0 | 10.0 |
| If-25 | 20.0 | 32.5 | 27.5 | 30.0 | 30.0 | 22.5 | 20.0 | 17.5 |
| If-26 | 5.0 | 12.5 | 5.0 | 2.5 | 2.5 | 5.0 | 5.0 | 5.0 |
| If-27 | 5.0 | 5.0 | 7.5 | 7.5 | 5.0 | 2.5 | 0.0 | 0.0 |
| If-28 | 52.8 | 47.2 | 47.2 | 47.2 | 36.1 | 27.8 | 25.0 | 25.0 |

Sweetness Ratings
0 = No sweetness;
25 = Slightly sweet;
50 = Just right;
75 = Slightly too sweet;
100 = Much too sweet

| Product # | During Brushing | After Brushing | 5 min | 10 min | 15 min | 20 min | 25 min | 30 min |
|---|---|---|---|---|---|---|---|---|
| If-1 | 52.5 | 57.5 | 37.5 | 27.5 | 12.5 | 10.0 | 7.5 | 7.5 |
| If-2 | 55.0 | 60.0 | 42.5 | 25.0 | 17.5 | 12.5 | 10.0 | 10.0 |
| If-3 | 37.5 | 52.5 | 47.5 | 32.5 | 17.5 | 15.0 | 7.5 | 7.5 |
| If-4 | 27.3 | 45.5 | 15.9 | 11.4 | 2.3 | 2.3 | 0.0 | 0.0 |
| If-5 | 25.0 | 30.0 | 22.5 | 10.0 | 7.5 | 7.5 | 7.5 | 5.0 |
| If-6 | 40.0 | 47.5 | 30.0 | 17.5 | 15.0 | 5.0 | 7.5 | 5.0 |
| If-7 | 32.5 | 50.0 | 42.5 | 20.0 | 12.5 | 7.5 | 2.5 | 2.5 |
| If-8 | 30.6 | 30.6 | 19.4 | 8.3 | 2.8 | 2.8 | 5.6 | 8.3 |
| If-9 | 42.5 | 47.5 | 27.5 | 15.0 | 12.5 | 5.0 | 5.0 | 5.6 |
| If-10 | 30.0 | 57.5 | 37.5 | 20.0 | 15.0 | 7.5 | 2.5 | 2.5 |
| If-11 | 45.5 | 52.3 | 31.8 | 20.5 | 9.1 | 4.5 | 2.3 | 2.3 |
| If-12 | 41.7 | 47.2 | 38.9 | 22.2 | 11.1 | 11.1 | 11.1 | 11.1 |
| If-13 | 7.5 | 20.0 | 10.0 | 10.0 | 10.0 | 10.0 | 7.5 | 7.5 |
| If-14 | 30.0 | 27.5 | 17.5 | 12.5 | 12.5 | 10.0 | 7.5 | 10.0 |
| If-15 | 19.4 | 44.4 | 25.0 | 16.7 | 5.6 | 5.6 | 5.6 | 5.6 |
| If-16 | 40.9 | 47.7 | 29.5 | 20.5 | 11.4 | 6.8 | 4.5 | 4.5 |
| If-17 | 40.0 | 50.0 | 35.0 | 25.0 | 20.0 | 10.0 | 5.0 | 5.0 |
| If-18 | 38.9 | 50.0 | 27.8 | 16.7 | 13.9 | 11.1 | 8.3 | 8.3 |
| If-19 | 35.0 | 37.5 | 25.0 | 15.0 | 7.5 | 5.0 | 5.0 | 5.0 |
| If-20 | 25.0 | 27.5 | 22.5 | 17.5 | 10.0 | 7.5 | 7.5 | 7.5 |
| If-21 | 42.5 | 52.5 | 25.0 | 15.0 | 10.0 | 10.0 | 10.0 | 7.5 |
| If-22 | 57.5 | 60.0 | 50.0 | 25.0 | 17.5 | 12.5 | 10.0 | 10.0 |
| If-23 | 40.0 | 50.0 | 35.0 | 22.5 | 15.0 | 7.5 | 5.0 | 2.5 |
| If-24 | 52.5 | 70.0 | 47.5 | 27.5 | 15.0 | 7.5 | 5.0 | 5.0 |
| If-25 | 50.0 | 67.5 | 40.0 | 20.0 | 17.5 | 10.0 | 10.0 | 10.0 |
| If-26 | 70.0 | 75.0 | 55.0 | 32.5 | 27.5 | 17.5 | 10.0 | 10.0 |
| If-27 | 52.5 | 60.0 | 42.5 | 25.0 | 15.0 | 5.0 | 5.0 | 5.0 |
| If-28 | 27.8 | 36.1 | 33.3 | 16.7 | 11.1 | 11.1 | 8.3 | 2.8 |

Bitterness Ratings
0 = No bitterness;
25 = Slightly bitter;
50 = Just right;
75 = Moderately bitter;
100 = Much too bitter

| Product # | During Brushing | After Brushing | 5 min | 10 min | 15 min | 20 min | 25 min | 30 min |
|---|---|---|---|---|---|---|---|---|
| If-1 | 72.5 | 75.0 | 75.0 | 70.0 | 62.5 | 55.0 | 52.8 | 52.5 |
| If-2 | 67.5 | 72.5 | 67.5 | 62.5 | 57.5 | 50.0 | 47.5 | 45.0 |

| Product # | During Brushing | After Brushing | 5 min | 10 min | 15 min | 20 min | 25 min | 30 min |
|---|---|---|---|---|---|---|---|---|
| If-3 | 72.5 | 75.0 | 75.0 | 75.0 | 70.0 | 57.5 | 52.5 | 50.0 |
| If-4 | 72.7 | 86.4 | 86.4 | 75.0 | 68.2 | 59.1 | 50.0 | 47.7 |
| If-5 | 72.5 | 75.0 | 72.5 | 65.0 | 57.5 | 52.5 | 50.0 | 47.5 |
| If-6 | 75.0 | 80.0 | 80.0 | 75.0 | 60.0 | 52.5 | 52.5 | 47.5 |
| If-7 | 75.0 | 85.0 | 75.0 | 65.0 | 60.0 | 50.0 | 45.0 | 47.5 |
| If-8 | 77.8 | 83.3 | 80.6 | 72.2 | 69.4 | 55.6 | 50.0 | 44.4 |
| If-9 | 75.0 | 85.0 | 85.0 | 80.0 | 75.0 | 72.5 | 60.0 | 58.3 |
| If-10 | 77.5 | 85.0 | 80.0 | 75.0 | 67.5 | 57.5 | 50.0 | 50.0 |
| If-11 | 75.0 | 79.5 | 75.0 | 63.6 | 63.6 | 54.5 | 47.7 | 45.5 |
| If-12 | 66.7 | 77.8 | 69.4 | 61.1 | 58.3 | 44.4 | 41.7 | 41.7 |
| If-13 | 87.5 | 92.5 | 90.0 | 87.5 | 82.5 | 70.0 | 65.0 | 55.0 |
| If-14 | 70.0 | 87.5 | 82.5 | 72.5 | 62.5 | 60.0 | 52.5 | 50.0 |
| If-15 | 80.6 | 94.4 | 91.7 | 86.1 | 77.8 | 63.9 | 55.6 | 55.6 |
| If-16 | 65.9 | 81.8 | 77.3 | 70.5 | 63.6 | 61.4 | 54.5 | 52.3 |
| If-17 | 67.5 | 72.5 | 70.0 | 65.0 | 60.0 | 60.0 | 55.0 | 55.0 |
| If-18 | 72.2 | 77.8 | 86.1 | 77.8 | 69.4 | 61.1 | 58.3 | 58.3 |
| If-19 | 70.0 | 87.5 | 82.5 | 75.0 | 62.5 | 57.5 | 52.5 | 52.8 |
| If-20 | 77.5 | 87.5 | 77.5 | 70.0 | 65.0 | 60.0 | 52.5 | 47.5 |
| If-21 | 67.5 | 80.0 | 77.5 | 67.5 | 67.5 | 62.5 | 57.5 | 55.0 |
| If-22 | 52.5 | 65.0 | 60.0 | 57.5 | 50.0 | 47.5 | 47.5 | 45.0 |
| If-23 | 67.5 | 77.5 | 80.0 | 72.5 | 60.0 | 55.0 | 50.0 | 47.5 |
| If-24 | 57.5 | 72.5 | 72.5 | 62.5 | 60.0 | 60.0 | 50.0 | 50.0 |
| If-25 | 65.0 | 80.0 | 72.5 | 75.0 | 67.5 | 65.0 | 55.0 | 50.0 |
| If-26 | 47.5 | 52.5 | 55.0 | 52.5 | 50.0 | 50.0 | 45.0 | 50.0 |
| If-27 | 52.5 | 65.0 | 65.0 | 60.0 | 50.0 | 47.5 | 42.5 | 42.5 |
| If-28 | 80.6 | 83.3 | 86.1 | 80.6 | 77.8 | 69.4 | 61.1 | 55.6 |

Freshness Ratings
0 = Very Stale;
25 = Slightly Stale;
50 = Neutral;
75 = Slightly Fresh;
100 = Very Fresh

| Product # | During Brushing | Immediately after rinsing | 5 min | 10 min | 15 min | 20 min | 25 min | 30 min |
|---|---|---|---|---|---|---|---|---|
| If-1 | 70.0 | 82.5 | 82.5 | 75.0 | 67.5 | 57.5 | 55.0 | 52.5 |
| If-2 | 72.5 | 77.5 | 80.0 | 72.5 | 70.0 | 62.5 | 57.5 | 52.5 |
| If-3 | 65.0 | 82.5 | 85.0 | 85.0 | 80.0 | 67.5 | 65.0 | 60.0 |
| If-4 | 75.0 | 79.5 | 79.5 | 72.7 | 70.5 | 65.9 | 63.6 | 63.6 |
| If-5 | 70.0 | 82.5 | 75.0 | 70.0 | 67.5 | 62.5 | 60.0 | 57.5 |
| If-6 | 72.5 | 80.0 | 82.5 | 77.5 | 72.5 | 70.0 | 60.0 | 57.5 |
| If-7 | 75.0 | 85.0 | 80.0 | 77.5 | 72.5 | 62.5 | 57.5 | 57.5 |
| If-8 | 80.6 | 91.7 | 80.6 | 75.0 | 75.0 | 66.7 | 55.6 | 52.8 |
| If-9 | 77.5 | 87.5 | 85.0 | 82.5 | 77.5 | 77.5 | 70.0 | 70.0 |
| If-10 | 77.5 | 85.0 | 82.5 | 75.0 | 72.5 | 70.0 | 60.0 | 60.0 |
| If-11 | 65.9 | 79.5 | 75.0 | 70.5 | 68.2 | 65.9 | 61.4 | 59.1 |
| If-12 | 75.0 | 86.1 | 86.1 | 77.8 | 72.2 | 63.9 | 61.1 | 62.5 |
| If-13 | 87.5 | 95.0 | 92.5 | 92.5 | 85.0 | 75.0 | 70.0 | 67.5 |
| If-14 | 80.0 | 95.0 | 85.0 | 75.0 | 67.5 | 60.0 | 60.0 | 57.5 |
| If-15 | 88.9 | 97.2 | 88.9 | 86.1 | 83.3 | 69.4 | 69.4 | 66.7 |
| If-16 | 72.7 | 75.0 | 79.5 | 79.5 | 68.2 | 61.4 | 59.1 | 61.4 |
| If-17 | 67.5 | 80.0 | 75.0 | 67.5 | 67.5 | 57.5 | 57.5 | 55.0 |
| If-18 | 75.0 | 84.4 | 78.1 | 78.1 | 68.8 | 68.8 | 62.5 | 59.4 |
| If-19 | 75.0 | 85.0 | 80.0 | 75.0 | 70.0 | 65.0 | 60.0 | 60.0 |
| If-20 | 75.0 | 85.0 | 80.0 | 72.5 | 65.0 | 57.5 | 55.0 | 52.5 |
| If-21 | 77.5 | 85.0 | 82.5 | 75.0 | 70.0 | 65.0 | 62.5 | 57.5 |
| If-22 | 60.0 | 65.0 | 65.0 | 62.5 | 57.5 | 57.5 | 55.0 | 55.0 |
| If-23 | 77.5 | 80.0 | 77.5 | 72.5 | 65.0 | 65.0 | 62.5 | 61.1 |
| If-24 | 72.5 | 75.0 | 80.0 | 72.5 | 65.0 | 60.0 | 57.5 | 57.5 |
| If-25 | 62.5 | 72.5 | 70.0 | 72.5 | 67.5 | 67.5 | 62.5 | 60.0 |
| If-26 | 55.0 | 57.5 | 65.0 | 62.5 | 62.5 | 65.0 | 62.5 | 62.5 |
| If-27 | 65.0 | 65.0 | 60.0 | 60.0 | 55.0 | 50.0 | 50.0 | 50.0 |
| If-28 | 77.8 | 80.6 | 80.6 | 77.8 | 75.0 | 72.2 | 63.9 | 58.3 |

Clean Feel Ratings
0 = Very Dirty Feeling;
25 = Slightly Dirty Feeling;
50 = Neutral;
75 = Slightly Clean Feeling;
100 = Very Clean Feeling

| Product # | During Brushing | After Brushing | 5 min | 10 min | 15 min | 20 min | 25 min | 30 min |
|---|---|---|---|---|---|---|---|---|
| If-1 | 32.5 | 30.0 | 37.5 | 40.0 | 45.0 | 45.0 | 42.5 | 42.5 |
| If-2 | 25.0 | 25.0 | 30.0 | 32.5 | 37.5 | 42.5 | 40.0 | 40.0 |
| If-3 | 35.0 | 27.5 | 33.3 | 40.0 | 42.5 | 45.0 | 45.0 | 47.5 |
| If-4 | 50.0 | 47.7 | 52.3 | 54.5 | 52.3 | 52.3 | 52.5 | 52.5 |
| If-5 | 47.5 | 40.0 | 42.5 | 42.5 | 40.0 | 37.5 | 45.0 | 45.0 |
| If-6 | 42.5 | 40.0 | 47.5 | 47.5 | 47.5 | 47.5 | 47.5 | 47.5 |
| If-7 | 37.5 | 32.5 | 37.5 | 45.0 | 47.5 | 47.5 | 50.0 | 50.0 |
| If-8 | 50.0 | 41.7 | 47.2 | 47.2 | 50.0 | 47.2 | 47.2 | 47.2 |
| If-9 | 30.0 | 32.5 | 37.5 | 42.5 | 47.5 | 50.0 | 47.5 | 47.5 |
| If-10 | 37.5 | 27.5 | 35.0 | 40.0 | 42.5 | 45.0 | 45.0 | 42.5 |
| If-11 | 27.3 | 22.7 | 40.9 | 38.6 | 40.9 | 40.9 | 40.9 | 43.2 |
| If-12 | 33.3 | 22.2 | 30.6 | 36.1 | 44.4 | 44.4 | 41.7 | 44.4 |
| If-13 | 67.5 | 62.5 | 67.5 | 67.5 | 60.0 | 55.0 | 50.0 | 50.0 |
| If-14 | 38.9 | 41.7 | 41.7 | 41.7 | 44.4 | 41.7 | 44.4 | 44.4 |
| If-15 | 55.6 | 44.4 | 50.0 | 50.0 | 50.0 | 52.8 | 47.2 | 47.2 |
| If-16 | 38.6 | 36.4 | 40.9 | 50.0 | 52.3 | 56.8 | 52.3 | 50.0 |
| If-17 | 30.0 | 25.0 | 32.5 | 32.5 | 40.0 | 47.5 | 47.5 | 47.5 |
| If-18 | 41.7 | 36.1 | 41.7 | 47.2 | 50.0 | 47.2 | 50.0 | 47.2 |
| If-19 | 45.0 | 40.0 | 40.0 | 45.0 | 45.0 | 42.5 | 42.5 | 45.0 |
| If-20 | 47.5 | 50.0 | 50.0 | 45.0 | 45.0 | 45.0 | 42.5 | 42.5 |
| If-21 | 37.5 | 37.5 | 42.5 | 50.0 | 52.5 | 45.0 | 40.0 | 45.0 |
| If-22 | 7.5 | 10.0 | 20.0 | 27.5 | 37.5 | 40.0 | 42.5 | 42.5 |
| If-23 | 20.0 | 15.0 | 22.5 | 30.0 | 30.0 | 37.5 | 37.5 | 37.5 |
| If-24 | 17.5 | 20.0 | 32.5 | 35.0 | 42.5 | 47.5 | 47.5 | 47.5 |
| If-25 | 25.0 | 22.5 | 38.9 | 47.5 | 47.5 | 47.5 | 45.0 | 42.5 |
| If-26 | 5.0 | 2.5 | 12.5 | 20.0 | 25.0 | 25.0 | 30.0 | 35.0 |
| If-27 | 12.5 | 7.5 | 12.5 | 20.0 | 30.0 | 32.5 | 37.5 | 35.0 |
| If-28 | 44.4 | 44.4 | 52.8 | 55.6 | 61.1 | 55.6 | 55.6 | 55.6 |

Taste Ratings
0 = Very Negative;
25 = Slightly Negative;
50 = Neutral;
75 = Slightly Positive;
100 = Very Positive The data showed that product #13 (saccharin:sucralose:rebiana in a 1:1:2 ratio) out performed all other combinations, including saccharin:sucralose combinations (product 20) and better than saccharin alone (products 1-3, and 19).

Example Product II

Metal Salt Containing Dentifrice

The dentifrices shown below are made using conventional methods; amounts are in weight %.

| Ingredient | IIA | IIB | IIC | IID | IIE |
|---|---|---|---|---|---|
| Calcium Carbonate | | | | 40.00 | |
| Binders | 1.00 | 1.8 | 1.00 | 1.00 | 0.20 |
| Thickeners | 2.00 | 1.00 | 1.25 | 0.4 | 0.8 |
| Color Solution (1%) | 0.05 | 0.05 | | | 0.175 |
| Dibasic Calcium Phosphate Dihydrate | | | 35.00 | | |
| Flavor[1] | 1.00 | 1.00 | 1.00 | 1.00 | 1.00 |
| Coolants | 0.03 | 0.24 | 0.20 | 0.50 | 0.58 |
| VBE | 0.01 | 0.01 | 0.01 | 0.01 | 0.01 |
| Glycerin USP | 16.489 | | 15.00 | | |
| Poloxamer 407 NF | | | | | 0.20 |
| Monosodium Ortho-phosphate | | | | | |
| Potassium Nitrate | 5.00 | | | | |
| Saccharin Sodium USP | 0.47 | 0.25 | 0.30 | 0.300 | 0.58 |
| Silica Abrasive | 24.00 | 12.50 | | | 17.00 |
| Sodium Lauryl Sulfate (27.9% soln) | 7.50 | 7.00 | 5.50 | 7.00 | 4.00 |
| NaOH 50% Solution | | | 1.00 | | |
| Sodium Monofluoro-phosphate | 0.76 | | 0.76 | 0.76 | 0.76 |
| Sodium Fluoride | | 0.32 | | | |
| Sodium Gluconate | | 1.00 | | | |
| Stannous Chloride Dihydrate | | 1.00 | | | |
| Zinc Citrate | | 0.50 | | | |
| Sodium Phosphate, Tribasic | 3.20 | | | | |
| Humectant | 10.50 | 33.00 | 12.00 | 14.00 | 57.00 |
| Tetra Sodium Pyro-phosphate, Anhydrous | | | 0.50 | 0.50 | 3.85 |
| Sodium Acid Pyrophosphate | | | | | 1.00 |
| Titanium Dioxide | 0.50 | 0.50 | | | 0.25 |
| Water, Purified, USP | QS | QS | QS | QS | QS |

| Ingredient | IIF | IIG | IIH | II | IIK |
|---|---|---|---|---|---|
| Calcium Carbonate | | | | 40.00 | |
| Binders | 1.00 | 1.8 | 1.00 | 1.00 | 0.20 |
| Thickeners | 0.5 | 1.00 | 1.25 | 0.4 | 0.8 |
| Color Solution (1%) | 0.05 | 0.05 | | | 0.175 |
| Dibasic Calcium Phosphate Dihydrate | | | 35.00 | | |
| Flavor[1] | 1.5 | 1.0 | 0.8 | 1.00 | 0.8 |
| Coolants | 0.5 | 0.2 | | 0.08 | |
| Glycerin USP | 16.489 | | 15.00 | | 0.10 |
| Potassium Nitrate | 5.00 | | | | |
| Sweetener Combinations | 0.47 | 0.25 | 0.30 | 0.300 | 0.58 |
| Silica Abrasive | 24.00 | 12.50 | | | 17.00 |
| Sodium Lauryl Sulfate (27.9% soln) | 7.50 | 7.00 | 5.50 | 7.00 | 4.00 |
| NaOH 50% Solution | | | 1.00 | | |
| Sodium Monofluoro-phosphate | 0.76 | | 0.76 | 0.76 | 0.76 |
| Sodium Fluoride | | 0.32 | | | |
| Sodium Gluconate | | 1.00 | | | |
| Stannous Chloride Dihydrate | | 1.00 | | | |
| Zinc Citrate | | 0.50 | | | |
| Sodium Phosphate, Tribasic | 3.20 | | | | |

-continued

| | | | | | |
|---|---|---|---|---|---|
| Humectant | 12.00 | 33.00 | 12.00 | 14.00 | 57.00 |
| Tetra Sodium Pyrophosphate, Anhydrous | | | 0.50 | 0.50 | 3.85 |
| Sodium Acid Pyrophosphate | | | | | 1.00 |
| Titanium Dioxide | 0.50 | 0.50 | | | 0.25 |
| Water, Purified, USP | QS | QS | QS | QS | QS |

[1]Flavor comprises about 31.3% menthol supplying about 500 ppm menthol.

Example Product III

Mouth Rinse Compositions

Mouth rinse compositions are made using conventional methods and are shown below with amounts of components in weight %.

| Ingredient | IIIA | IIIB | IIIC |
|---|---|---|---|
| Ethanol, USP 190 proof | 15.000 | 15.000 | 15.000 |
| Glycerin | 7.500 | 7.500 | 7.500 |
| Polysorbate 80, NF | 0.120 | 0.120 | 0.120 |
| Flavor | 0.160 | 0.160 | 0.160 |
| Sweetener Combinations | 0.1 | 0.1 | 0.060 |
| Color Solution | 0.040 | 0.040 | 0.040 |
| Cetylpyridinium Chloride | 0.045 | 0.045 | 0.045 |
| Benzoic Acid | 0.005 | 0.005 | 0.005 |
| Sodium Benzoate | 0.054 | 0.054 | 0.054 |
| Water | QS | QS | QS |

Example Product IV

Peroxide Mouth Rinse Compositions

Peroxide-containing mouth rinse compositions are shown below with amounts of components in weight %. These compositions are made using conventional methods. They provide a pleasant high-impact minty taste during use and noticeable long-lasting fresh breath.

| Ingredient | IVA | IVB | IVC | IVD | IVE | IVF |
|---|---|---|---|---|---|---|
| 35% $H_2O_2$ solution | 4.286 | 4.286 | 4.286 | 2.143 | 4.286 | 4.286 |
| Coolant | 0.075 | 0.02 | 0.04 | 0.04 | 0.03 | 0.04 |
| Flavor | 0.145 | 0.135 | 0.135 | 0.15 | 0.135 | 0.135 |
| Calcium Chloride | 0.025 | | 0.025 | 0.02 | 0.025 | 0.025 |
| Poloxamer 407 | 0.75 | 0.75 | 0.750 | 0.10 | 0.10 | 0.10 |
| Glycerin | 11.00 | 11.00 | 11.00 | 20.00 | 20.00 | 20.00 |
| Propylene Glycol | 3.00 | 3.00 | | 4.00 | 4.00 | 4.00 |
| Sweetener Combinations | 0.08 | — | 0.068 | 0.06 | 0.08 | 0.06 |
| Polyphosphate | | | 1.00 | | | |
| Phytic Acid | | 2.00 | | | | |
| Cetyl Pyridinium Chloride | | | | 0.074 | 0.10 | 0.10 |
| Na Citrate | 0.212 | 0.212 | | | | |
| Citric Acid | 0.052 | 0.052 | 0.052 | | | |
| Alcohol, USP | | | 5.00 | | | |
| Water, Purified, USP | QS | QS | QS | QS | QS | QS |

Example Product V

Tartar Control Dentifrice compositions

The dentifrices shown below are made using conventional methods; amounts are in weight %.

| Ingredient | VA | VB | VC | VD | VE |
|---|---|---|---|---|---|
| Calcium Peroxide FCC | | | 0.10 | | |
| Thickener | 5.0 | 2.5 | 4.5 | 0.80 | 5.0 |
| Binder | 0.60 | 0.75 | 0.40 | 0.45 | 0.70 |
| Polymer | | | 0.20 | | |
| Color Solution (1%) | 0.05 | 0.05 | 0.50 | 0.75 | 0.175 |
| Flavor | | | | | 0.15 |
| Coolant | | | 0.02 | 0.05 | 0.02 |
| Glycerin USP 99.7% | 9.00 | 11.85 | 33.164 | 9.00 | |
| Poloxamer 407 NF | | | 1.00 | | 0.20 |
| Tetra Potassium Pyrophosphate (60% Soln) | 6.38 | | | | |
| Propylene Glycol USP Crest | | | 10.00 | | |
| Sweetener Combinations | 0.46 | 0.50 | 0.45 | 0.40 | 0.58 |
| Sodium Acid Pyrophosphate | 2.10 | | | 4.00 | 1.00 |
| Silica Abrasive | 22.00 | 31.00 | 20.00 | 21.00 | 17.00 |
| Silica Thickening | | | 2.00 | | |
| Sodium Bicarbonate USP | | 1.50 | 9.00 | | |
| Sodium Carbonate Anhydrous NF | | 0.50 | | | |
| Sodium Hydroxide 50% Solution | | | 1.74 | 2.20 | |
| Sodium Lauryl Sulfate (27.9% soln) | 4.00 | 5.00 | 3.00 | 4.00 | 4.00 |
| Sodium Monofluorophosphate | 0.76 | 0.76 | 0.76 | 0.76 | 0.76 |
| Sorbitol Solution USP | 24.28 | 24.54 | 3.985 | 44.686 | 56.885 |
| Tetra Sodium Pyrophosphate, Anhydrous | 2.05 | 5.045 | 3.85 | | 3.85 |
| Titanium Dioxide | 0.50 | | 1.00 | | 0.25 |
| Titanium Dioxide/ Carnauba Wax Prills | | 0.60 | | 0.30 | |
| Water, Purified, USP | QS | QS | QS | QS | QS |

Example

Consumer Test #2

The data in the table below was from a 146 person panel where products were delivered in a dentifrice as made in Example V. Seven products were randomized and evaluated by the panelists in a sequential monadic fashion over the course of one week. Respondents brushed up to twice per day (once in AM and once in PM) and then filled out a self-administered computerized questionnaire. Approximately 1.0 gram of product was used per brushing. Dentifrice (d) contains the same ratio of sweeteners as the product in Consumer Test #1.

| Total Base Size: 146 | (a) | (b) | (c) | (d) |
|---|---|---|---|---|
| Saccharin level | 0.4% | — | 0.2% | 0.1% |
| Sucralose level | — | — | — | 0.2% |

-continued

| Total Base Size: 146 | (a) | (b) | (c) | (d) |
|---|---|---|---|---|
| REBIANA level | — | 0.4% | 0.2% | 0.2% |
| | | Ratings (0-100 scale where 0 = Poor, 100 = Excellent) | | |
| Overall Rating | 69b | 62 | 71b | 78abc |
| Minty Taste While Brushing | 64b | 54 | 67b | 74ab |
| Flavor Intensity While Brushing | 61b | 51 | 62b | 72abc |
| Sweetness Intensity While Brushing | 62b | 50 | 64b | 72abc |
| Amount of Cooling | 69 | 64 | 72b | 74b |
| Can Feel the Product Working | 67 | 62 | 69b | 74ab |
| Product Texture | 71 | 68 | 72 | 78ab |
| Product Foam/Suds | 64 | 60 | 70b | 73ab |
| Is New and Different | 55 | 52 | 57 | 63ab |
| Is a Good Value | 60 | 54 | 61b | 68abc |
| Is a Quality Product | 66b | 58 | 66b | 74abc |
| Prevents Cavities | 66 | 61 | 67b | 70b |
| Prevents Tartar | 64 | 61 | 64 | 68b |
| Strengthens Enamel | 62 | 58 | 64b | 67b |
| Prevents Stains | 64 | 60 | 64 | 69b |
| Teeth Look Whiter | 62 | 57 | 62 | 65b |
| Removes Surface Stains | 65 | 59 | 64 | 68b |
| Mouth Feels Moist | 62 | 59 | 65 | 69ab |
| Thoroughly Cleans Teeth | 70 | 64 | 70 | 74b |
| Leaves Mouth Feeling Clean | 72 | 67 | 73b | 76b |
| Keeps Mouth Healthy | 68 | 63 | 68 | 72b |
| Ease of Rinsing | 71 | 65 | 73b | 75b |
| No Film/Residue Remaining on Teeth | 70 | 67 | 72 | 77ab |

Dentifrice (d) was statistically better than all other dentifrices in the test - providing higher overall rating preference, minty taste, flavor intensity, sweetness impression, and on value and quality.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sweetener composition comprising:
    A) saccharin;
    B) sucralose; and
    C) rebaudioside A;
wherein the saccharin, sucralose and the rebaudioside A are in a ratio of about 1:1:2.

2. A sweetener composition according to claim 1 wherein the composition comprises, in total, from 20% to 100% of saccharin, sucralose, and rebaudioside A.

3. A sweetener composition according to claim 1 wherein the composition comprises, in total, from 50% to 100% of saccharin, sucralose, and rebaudioside A.

4. A sweetener composition consisting essentially of:
    A) saccharin;
    B) sucralose; and
    C) rebaudioside A;
wherein the saccharin, sucralose and the rebaudioside A are in a ratio of about 1:1:2.

5. An oral composition comprising:
    a) sweetener composition of claim 1; and
    b) one or more orally acceptable carrier materials.

6. An oral composition comprising:
    a) sweetener composition of claim 4; and
    b) one or more orally acceptable carrier materials.

7. An oral composition according to claim 5 wherein the composition comprises from 0.001% to 4%, of the sweetener composition.

8. An oral composition according to claim 7 wherein the composition comprises from 0.01% to 3%, of the sweetener composition.

9. An oral composition according to claim 5, further comprising a metal salt selected from zinc salts, stannous salts, copper salts, strontium salts, and mixtures thereof.

10. An oral composition according to claim 6, further comprising a metal salt selected from zinc salts, stannous salts, copper salts, strontium salts, and mixtures thereof.

11. An oral composition according to claim 5 wherein the composition comprises 0.1% saccharin, 0.1% sucralose and 0.2% rebaudioside A.

12. An oral composition according to claim 5 wherein the oral composition further comprises a surfactant.

13. An oral composition according to claim 5 wherein the oral composition further comprises an active.

* * * * *